United States Patent [19]
Schwanke et al.

[11] Patent Number: 4,971,774
[45] Date of Patent: Nov. 20, 1990

[54] STERILIZING CONTAINER FOR SURGICAL INSTRUMENTS

[75] Inventors: Wolfgang Schwanke, Weilheim; Wolfgang Taschner, Tuttlingen, both of Fed. Rep. of Germany

[73] Assignee: Aesculap AG, Tuttlingen, Fed. Rep. of Germany

[21] Appl. No.: 283,955

[22] PCT Filed: Mar. 26, 1988

[86] PCT No.: PCT/EP88/00257
  § 371 Date: Oct. 17, 1988
  § 102(e) Date: Oct. 17, 1988

[30] Foreign Application Priority Data
  Apr. 3, 1987 [DE] Fed. Rep. of Germany ....... 3711271

[51] Int. Cl.$^5$ ............ A61L 2/26; A61L 2/06; A91B 19/02
[52] U.S. Cl. .................... 422/310; 422/295; 422/296; 220/358; 220/361; 220/366; 220/378
[58] Field of Search ............ 422/310, 295, 296; 220/358, 361, 366, 378

[56] References Cited
U.S. PATENT DOCUMENTS
4,512,498 4/1985 Leibinger ............ 220/366 X
4,551,311 11/1985 Lorenz ............ 422/310 X FOREIGN PATENT DOCUMENTS
2839219 3/1980 Fed. Rep. of Germany .
3407112 9/1985 Fed. Rep. of Germany .
8704981 8/1987 Fed. Rep. of Germany .

Primary Examiner—Robert J. Warden
Assistant Examiner—Lynn M. Kummert
Attorney, Agent, or Firm—Kramer, Brufsky & Cifelli

[57] ABSTRACT

In a sterilizing container for surgical instruments comprising a bottom part and a lid sealingly positionable thereon, with a seal made of an elastically deformable material extending around the lid along the outer circumference thereof and being fixed to the lid by means of a profiled strip, in order to effect a simplified attachment of the profiled strip to the lid without changing the lid, it is proposed that the profiled strip consist of a plastic material with a hard rating and be adhesively bonded to the inside of the lid.

14 Claims, 1 Drawing Sheet

U.S. Patent    Nov. 20, 1990    4,971,774
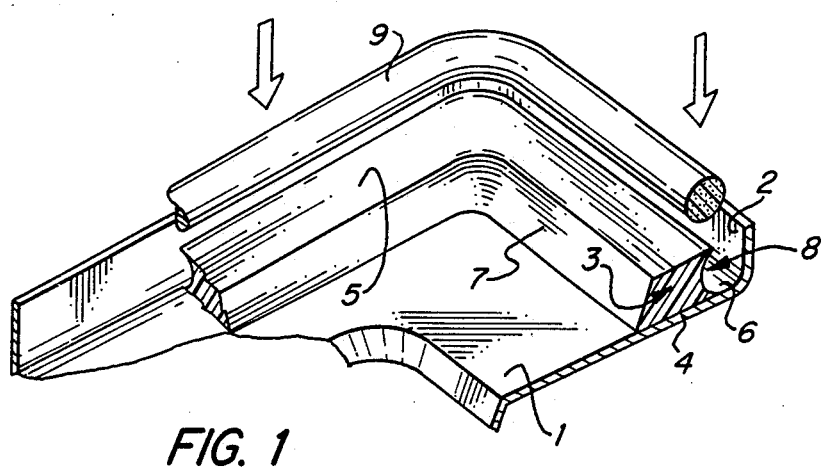
FIG. 1
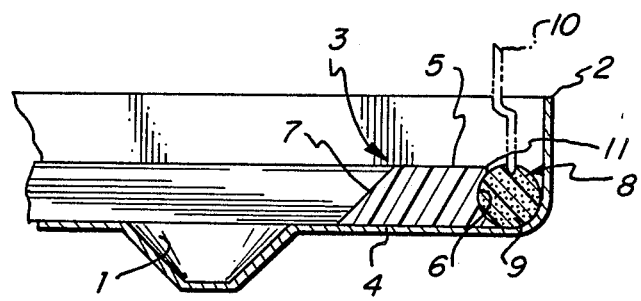
FIG. 2
FIG. 3
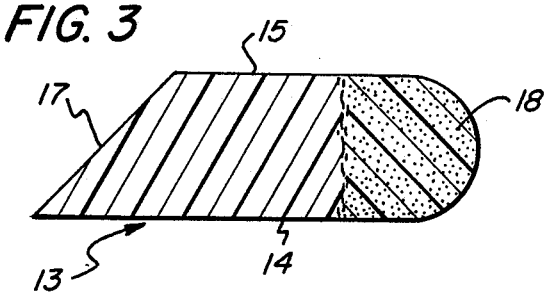

STERILIZING CONTAINER FOR SURGICAL INSTRUMENTS

The invention relates to a sterilizing container for surgical instruments or the like comprising a bottom part and a lid sealingly positionable thereon, with a seal made of an elastically deformable material extending around the lid along the outer circumference thereof and being fixed to the lid by means of a profiled strip.

Sterilizing containers of this kind are, for example, known from German Patent No. 3 407 112.

The profiled strip used to hold the seal in the known design is a metal section which is riveted to the lid. Aside from the expenditure involved in making the rivet joint, for which purpose bores must be made in the lid, the riveted joint also causes a change in the lid surface as the rivets normally protrude beyond the lid surface.

In other known lid seals, the lid is deformed in such a manner as to form a groove for accommodation of a band-shaped seal on the inside. This type of manufacture, too, is elaborate and results in a change in the lid surface.

The object of the invention is to so improve a sterilizing container of the generic kind that it is possible to fix a soft seal on the inside in a simple manner without changes having to be made to the lid for this purpose.

This object is accomplished in a sterilizing container of the kind described at the beginning, in accordance with the invention, by the profiled strip consisting of a plastic material with a hard rating and being adhesively bonded to the inside of the lid.

Such a profiled plastic strip may be attached to the lid simply by adhesive bonding or cold vulcanization without the lid having to be worked in a special manner.

In a preferred embodiment of the invention, provision is made for the profiled strip to form between itself and a downwardly drawn rim of the lid an insertion groove for the seal in which the seal is held by frictional or positive connection. Hence the seal is not held by the profiled strip alone, but rather the rim of the lid is simultaneously used as part of a holder for the seal.

In this case, it is particularly advantageous for the insertion groove to be undercut in order to secure the seal. This then ensures safe fixing of the seal, yet the seal can be easily inserted and exchanged.

Insertion may be facilitated by the profiled strip according to a further preferred embodiment of the invention slanting downwardly towards the insertion groove.

It is particularly expedient for the seal to be of circular cross-section and for the profiled strip to be of arcuate cross-section towards the insertion groove.

In a further preferred embodiment, provision may be made for the profiled strip itself to comprise an area of plastic material with a soft rating which forms the seal. A seal in the form of a separate part is then not used, but instead the profiled strip itself forms the seal with its soft rated area.

In a first preferred embodiment, provision is made for the area with a soft rating to be injected onto or adhesively bonded to the profiled strip area of plastic material with a hard rating.

In accordance with another embodiment, however, provision may also be made for the soft rated area and the hard rated area of the profiled strip to be of integral design, more particularly, the hardness may decrease continuously from the hard rated to the soft rated area.

A particularly well suited material for the profiled strip is silicon rubber. The seal or the soft rated area of the profiled strip may preferably consist of a plastic foam, in particular, of porous silicon rubber.

The plastic material with a hard rating may have Shore hardnesses of between 70 and 90, whereas Shore hardnesses of between 10 and 30 are expedient for the seal or the soft rated area of the profiled strip.

Particularly good fixing of the profiled strip on the lid is obtained by the profiled strip having a plane bonding surface which rests against the lid.

It is, furthermore, advantageous for the profiled strip to slant downwardly on its side remote from the seal, thereby forming an acute angle between the downwardly slanting side and the bonding surface. Cleaning by wiping is thereby facilitated and, on the other hand, optimum adhesion is obtained on the inside of the lid in the area of transition between the bonding surface and the side surface as the profiled strip is of tongue-type design in this area and rests with a close fit against the inside surface of the lid.

The following description of preferred embodiments of the invention serves in conjunction with the drawings to explain the invention in more detail. The drawings show:

FIG. 1 a perspective, partial view of a lid with a cord-shaped seal prior to insertion into the insertion groove;

FIG. 2 a partial, sectional view of the lid of FIG. 1 with the seal inserted therein; and FIG. 3 a sectional view of a profiled strip with an integrated sealing area.

A sterilizing container for accommodating surgical instruments or the like comprises a tub-shaped bottom part with a bottom and side walls which are not illustrated in the drawings. A substantially plane lid 1 with downwardly drawn, circumferential rims 2 is placed on this bottom part. Tub and lid consist, for example, of sheet aluminum.

A profiled strip 3 which extends parallel to the rims 2 and, in the embodiment of FIGS. 1 and 2, comprises a plane bonding surface 4 resting against the inside of the lid 1, an underside 5 extending parallel to the bonding surface 4, a boundary surface 6 of arcuate cross-section facing the rim 2 of the lid 1 and an inner side surface 7 extending at an acute angle to the bonding surface 4 is inserted in the lid 1 in order to seal the lid 1 relative to the bottom part. The boundary surface 6 is spaced from the rim 2 and forms together with the rim 2 and the corner region of the lid 1 an insertion groove 8 for a cord-shaped endless seal 9. This endless seal 9 may be pressed into the insertion groove 8, whereby it undergoes deformation, and is held in the insertion groove 8 by virtue of the undercut of the boundary surface 6 of arcuate configuration (FIG. 2). Therefore, when the lid is put on, the seal 9 sealingly embraces the top edge of the side wall 10 of the bottom part.

In order to facilitate insertion of the endless seal 9 into the insertion groove 8, the profiled strip 3 has an insertion surface 11 which slants downwardly towards the insertion groove 8.

The profiled strip 3 consists of a plastic material with a hard rating, for example, hard rubber or silicon with a Shore hardness of the order of between 70 and 90, preferably 80. It is attached to the inside of the lid 1 by adhesive bonding by means of a suitable adhesive applied in a thin layer to the bonding surface 4 or by cold vulcanization. Therefore, no changes to the lid are necessary in order to fix the profiled strip on the lid.

In the modified embodiment illustrated in FIG. 3, the profiled strip 13 comprises in the same manner a plane bonding surface 14, an underside 15 extending parallel to the bonding surface 14 and a side surface 17 forming an acute angle with the bonding surface 14. On the side opposite the side surface 17, however, the profiled strip 13 merges into a sealing area 18 of rounded crosssection which has a substantially softer rating than the remainder of the profiled strip. This sealing area 18 may, for example, have a Shore hardness of between 10 and 30, whereas the remainder of the profiled strip 13 has a Shore hardness of between 10 and 90, preferably 80. In this case, too, the entire profiled strip including the sealing area 18 consists of an elastomeric plastic material, for example, silicon.

The sealing area 18 may be adhesively bonded to or injected onto the remainder of the profiled strip 13. It is, however, also possible for the profiled strip 13 including the sealing area 18 to be of integral design, in which case, the transition from an area of high hardness to the area of lower hardness may be continuous or discontinuous.

The sealing area 18 may be of porous design. This part may, for example, be of expanded rubber-type quality.

The profiled strip 13 shown in FIG. 3 is adhesively bonded to the inside of the lid by means of a suitable adhesive in the same manner as the profiled strip 3 of FIGS. 1 and 2. In this case, the adhesive may be the same substance as that of which the profiled strip 13 consists, i.e., for example, liquid silicon.

We claim:

1. Sterilizing container for surgical instruments comprising a bottom part and a lid sealingly positionable thereon, with a seal made of an elastically deformable material extending around the lid along the outer circumference thereof and being fixed to the lid by means of a profiled strip, wherein the profiled strip (3; 13) consists of a plastic material with a hard rating and is adhesively bonded to the inside of the lid.

2. Container as defined in claim 1, wherein the profiled strip (3) and a downwardly drawn lid rim (2) form an insertion groove (8) for the seal (9) therebetween in which the seal (9) is held by frictional or positive connection.

3. Container as defined in claim 2, wherein the insertion groove (8) is undercut in order to secure the seal (9).

4. Container as defined in one of claim 2 wherein the profiled strip (3) slants downwardly towards the insertion groove (8).

5. Container as defined in claim 2, wherein the seal (9) is of circular cross-section and the profiled strip (3) is of arcuate cross section adjacent the insertion groove (8).

6. Container as defined in claim 1, wherein the profiled strip (13) has an area (18) of plastic material with a soft rating which forms the seal.

7. Container as defined in claim 6, wherein the area (18) with a soft rating is injected onto or adhesively bonded to the area of the profiled strip (13) which is made of plastic material with a hard rating.

8. Container as defined in claim 6, wherein the area (18) with a soft rating and the area of the profiled strip (13) with a hard rating are of integral design.

9. Container as defined in claim 1, wherein the profiled strip (3;13) consists of silicon rubber.

10. Container as defined in claim 1, wherein the seal (9) or the soft rated area (18) of the profiled strip (13) consists of a plastic foam.

11. Container as defined in claim 1, wherein the plastic material with a hard rating has a Shore hardness of between 70 and 90.

12. Container as defined in claim 1, wherein the seal (9) or the soft rated area (18) of the profiled strip (13) has a Shore hardness of between 10 and 30.

13. Container as defined in claim 1, wherein the profiled strip (3,13) has a plane bonding surface (4; 14) which rests against the lid (1).

14. Container as defined in claim 1, wherein the profiled strip (3;13) slants downwardly on a side thereof (7, 17) remote from the seal (9; 18), thereby forming an acute angle between the downwardly slanting side (7; 17) and the bonding surface (4; 14).

* * * * *
* * * * *

UNITED STATES PATENT AND TRADEMARK OFFICE
CERTIFICATE OF CORRECTION

PATENT NO. : 4,971,774

DATED : November 20, 1990

INVENTOR(S) : Wolfgang Schwanke, et al.

It is certified that error appears in the above-identified patent and that said Letters Patent is hereby corrected as shown below:

In Claim 4, column 4, line 7, delete "one of".

Signed and Sealed this

Seventh Day of April, 1992

Attest:

HARRY F. MANBECK, JR.

*Attesting Officer*      *Commissioner of Patents and Trademarks*